(12) United States Patent
Marchesi

(10) Patent No.: US 11,353,366 B2
(45) Date of Patent: Jun. 7, 2022

(54) METHOD FOR PRODUCING A TEXTILE SENSOR

(71) Applicant: PLUG & WEAR SRL, Florence (IT)

(72) Inventor: Riccardo Marchesi, Vaglia (IT)

(73) Assignee: KNITRONIX S.R.L., Florence (IT)

( * ) Notice: Subject to any disclaimer, the term of this patent is extended or adjusted under 35 U.S.C. 154(b) by 609 days.

(21) Appl. No.: 16/331,287

(22) PCT Filed: Sep. 20, 2017

(86) PCT No.: PCT/IB2017/055706
§ 371 (c)(1),
(2) Date: Mar. 7, 2019

(87) PCT Pub. No.: WO2018/055529
PCT Pub. Date: Mar. 29, 2018

(65) Prior Publication Data
US 2019/0353533 A1 Nov. 21, 2019

(30) Foreign Application Priority Data
Sep. 20, 2016 (IT) .................. 102016000094342

(51) Int. Cl.
*G01K 7/18* (2006.01)
*D04B 1/14* (2006.01)
(Continued)

(52) U.S. Cl.
CPC .............. *G01K 7/18* (2013.01); *D04B 1/14* (2013.01); *D04B 21/14* (2013.01); *G01K 1/14* (2013.01);
(Continued)

(58) Field of Classification Search
CPC ... H01C 7/06; G01K 7/18; G01K 1/14; D04B 1/14; D04B 21/14
See application file for complete search history.

(56) References Cited

U.S. PATENT DOCUMENTS 4,659,873 A * 4/1987 Gibson .................. H01H 3/141
178/18.05
5,613,377 A * 3/1997 Marchesi ............... D04B 1/126
139/434
(Continued)

FOREIGN PATENT DOCUMENTS

DE 19927686 A1 3/2001
KR 20110050610 A 5/2011

OTHER PUBLICATIONS

International Search Report, dated Dec. 18, 2017, corresponding to Application No. PCT/IB2017/055706.
(Continued)

*Primary Examiner* — Kyung S Lee
(74) *Attorney, Agent, or Firm* — Ladas & Parry LLP; Malcolm J. MacDonald

(57) ABSTRACT

A method for manufacturing a textile temperature sensor, including arranging a linear knitting machine having a first thread-guide and a second thread-guide; arranging a conductive insulated wire on the first thread-guide; meshing the conductive insulated wire for making a mesh portion B having a nonconductive surface; arranging an electric resistance measuring device configured to measure a variation of electric resistance, the electric resistance being a function of the temperature; the measuring device phase of the electric resistance including a first electric cable and a second electric cable; electric connection of the first electric cable to the first end and of the second electric cable to the second end; and arranging a control unit arranged to receive from the device the variation of electric resistance in order to calculate excursions of the temperature at the lead wire.

13 Claims, 5 Drawing Sheets

(51) Int. Cl.
*D04B 21/14* (2006.01)
*G01K 1/14* (2021.01)
*H01B 1/12* (2006.01)
*H01C 7/06* (2006.01)

(52) U.S. Cl.
CPC ............... *H01B 1/124* (2013.01); *H01C 7/06* (2013.01); *D10B 2403/02431* (2013.01)

(56) References Cited

U.S. PATENT DOCUMENTS

| | | | | |
|---|---|---|---|---|
| 6,073,466 | A * | 6/2000 | Marchesi | D04B 1/24 66/145 S |
| 10,519,575 | B2 * | 12/2019 | Thompson | D03D 1/0088 |
| 10,591,273 | B2 * | 3/2020 | Veca | B60N 2/002 |
| 10,934,639 | B2 * | 3/2021 | Horter | D03D 11/00 |
| 2005/0062486 | A1 | 3/2005 | Qi et al. | |
| 2007/0171024 | A1 * | 7/2007 | Yang | A61B 5/6805 338/2 |
| 2007/0210490 | A1 * | 9/2007 | Malloy | D03D 15/593 264/425 |
| 2008/0233822 | A1 * | 9/2008 | Swallow | H05K 3/10 442/185 |
| 2014/0026678 | A1 | 1/2014 | Cannard et al. | |

OTHER PUBLICATIONS

Muhammad Dawood Husain et al., "Effect of Strain and Humidity on the Performance of Temperature Sensing Fabric", International Journal of Textile Science, vol. 2, No. 4, 2013, pp. 105-112, XP055365030.

Muhammad Dawood Husain, "Development of Temperature Sensing Fabric", Ph.D. Thesis, The University of Manchester, 2012, pp. 1-277.

* cited by examiner

METHOD FOR PRODUCING A TEXTILE SENSOR

FIELD OF THE INVENTION

The present invention relates to the field of thermistors, i.e. of the temperature sensors that exploit the variation of the resistivity of some materials at temperature variation.

In particular, the invention relates to a textile thermistor.

DESCRIPTION OF THE PRIOR ART

A thermistor, or resistance thermometer, is a temperature sensor that exploits the variation of the resistivity of some materials at temperature variation.

As well known, the resistance R generated by a conductive wire when current is passing is related to the resistivity of the material ρ according to the law $$R = \rho * \frac{l}{A},$$

where l e A are, respectively, length and section of the conductive wire.

Furthermore, for metals exists a linear equation that links resistivity and temperature:

$$\rho(T) = \rho_0 * [1 + \alpha(T-T_0)]$$

Wherein:
T is the temperature;
$\rho(T)$ is the resistivity of the material to the temperature T;
$\rho_0$ is the resistivity of the material to the temperature $T_0$;
$\alpha$ is a coefficient that depends upon the material.
It is therefore possible to write:

$$R(T) = \rho(T) * \frac{l}{A} = \rho_0 * \frac{l}{A} * [1 + \alpha(T - T_0)]$$

From which, known the geometric parameters and known the material, it is possible to determine the temperature excursion ($T-T_0$) starting from the resistance R(T) measured on conductive wire.

As evident by the previous equation, for the same material ($\rho_0$ and $\alpha$ constant), higher is the ratio $$\frac{l}{A}$$

the greater is the value of R(T) generated by a same temperature excursion ($T-T_0$). Then, by increasing l and reducing A, there is a higher sensitivity of the thermistor.

The remarkable versatility and precision of thermistors has allowed in the last years a big development of this technology, especially in industry.

In particular, by inserting a resistive metal wire in a tissue, it is possible to exploit the technology of thermistor for making a flexible and wearable element that allows to measure the surrounding temperature.

In the thesis "*Development of temperature sensing fabric*" presented to the University of Cambridge in the 2012, Muhammad Dawood Husain presents a heat-resistant fabric where the resistive metal fibers are inserted directly by the textile machine that produces the fabric itself. In this case, the textile machine is a linear knitting machine that produces a flat knit fabric. With reference to FIG. 1, the introduction of the metal fibers is carried out by weaving, i.e. interposing the metal wire 20 between the knitting rows 10 of the fabric. This way, the metal wire 20 remains in embedded in the fabric and, once connected its ends to the resistance measuring instrument, it is possible to measure the temperature at which the textile sensor is subjected.

However, this exemplary embodiment has some drawbacks.

Firstly, it has a limited wire length l. In fact, despite the wire is stretched in the fabric by crossing many times, the maximum wire length is equal to $n*W_s+L_a$, where n is the number of fabric knitting rows, $W_s$ is the fabric width and $L_a$ is the fabric.

Secondly, there is a limitation on the number of inserts per unit of surface. One of the methods that could be used for increasing the length of the wire is to decrease the length of the knitting rows, thus increasing the number of rows for length unit of the fabric. Such method however is not obtainable if the wire is not enameled with an insulator since, in the use of the fabric, the woven branches of conductive wire could contact each other and causing short circuits, and then false measurements. The platinum wire is not in fact available enameled, whereas the wire copper is. The replacement of the platinum wire with an enameled wire brings cost benefits, but it introduces drawbacks concerning sensitivity, since the coefficient of temperature of the copper is much lower than the platinum.

Another drawback is the limitation on the diameter of the conductive wire. In the thesis above cited, the structure of the fabric is done by horizontal weaving. This means that the metal wire, not meshed, is located between two knitting rows. When the fabric is subjected to traction, the textile wire is resiliently deforms, whereas the metal wire is much rigid and, if the section of the wire A is too small, the wire may break, irreversibly damaging the thermometer.

Furthermore, always owing to the different elasticity between fabric and metal wire due to the weaving, you have problems also immediately after generating the fabric. Once formed the fabric, in fact, it tends to retreat in the direction of the weft, whereas the metal wire doesn't. With reference to FIG. 2A, there are formed therefore side slots 25 of metal wire 20 that protrude from the fabric texture, that, in addition to provide an imperfection, can also cause a break of the wire if the side slot is engages in some object during the use of the fabric.

Finally, there is a difficulty to connect the end of the conductive wire to a conductive cable of larger diameter, which can be used for connecting the device to a data acquisition card.

SUMMARY OF THE INVENTION

It is therefore a feature of the present invention to provide a method for manufacturing a textile temperature sensor which allows to increase the length of the wire and to decrease the section with respect to the prior art, so as to obtain a better sensitivity in temperature detection.

It is also a feature of the present invention to provide such a method that makes it possible to obtain a fabric more resilient and deformable with respect to the prior art.

These and other objects are achieved by a method for manufacturing a textile temperature sensor, said method comprising the steps of:

arranging a linear knitting machine comprising at least one first thread-guide and a second thread-guide;

arranging a conductive insulated wire on the first thread-guide, said conductive insulated wire having a first end and a second end;

meshing the conductive insulated wire for making at least one mesh portion B having not conductive surface;

arranging an electric resistance measuring device configured to measure a variation of electric resistance R(T), said electric resistance R(T) being function of the temperature T, said electric resistance measuring device comprising a first electric cable and a second electric cable;

electric connection of the first electric cable to the first end and of the second electric cable to the second end;

arranging a control unit arranged to receive from the device the variation of electric resistance R(T) in order to calculate excursions of temperature T at the conductive wire;

whose main feature is that it also comprises the steps of:

arranging a non-insulated conductive wire on the second thread-guide;

meshing simultaneously the conductive insulated wire with a non-insulated conductive wire for making two mesh portions A and C, said mesh portions A and C having, conductive surfaces;

connecting the conductive insulated wire with the non-insulated conductive wire for connecting electrically the first end to the mesh portion A and the second end to the mesh portion C;

and that the step of electric connection of the first electric cable to the first end and of the second electric cable to the second end is carried out connecting, respectively, the first electric cable to the mesh portion A and the second electric cable to the mesh portion C.

Advantageously, are also provided the steps of:

arranging a textile wire on a third thread-guide the linear knitting machine;

meshing simultaneously the textile wire with the conductive insulated wire at the at least one mesh portion B.

Owing to the meshing technique with which the conductive insulated wire and the textile wire are woven, the thermoresistive sensor of the present invention has relevant advantages with respect to prior art, where the wires were instead woven by means of weaving technique.

Firstly, thermistor has a much higher sensitivity. In fact, owing to the meshing the wires, the conductive insulated wire is substantially overlapped to the textile wire in all the mesh portion, and it has then a length l much higher than the fabric of the prior art. Furthermore, just because the wires follow the same path, the conductive insulated wire is better supported by the textile wire, which can withstand the strains caused by any deformations or tissue traces. Such determines a cross section A of the conductive insulated wire smaller than the prior art. As previously mentioned, increasing l and decreasing A, there is an increase of the sensitivity of the thermoresistive sensor.

Secondly, there is the removal of the side slots that are formed in the woven tissue of the prior art, owing to the retraction of the fabric.

Finally, there is an overall increase of the elasticity of the fabric in the direction of the weft, due to the fact that the conductive insulated wire is arranged according to the knots of the mesh, creating slots, and it is not woven parallel to the direction of the weft. In case of tension of the fabric in the direction of the weft, the side slots extend allowing the yielding of the fabric and its subsequent return to the original shape once the mechanical stress has been completed.

Advantageously, the insulated wire has a diameter set between 10 µm and 150 µm.

The conductive wire is, for example, made of copper.

The textile wire is, for example, made in polyester. Alternatively, the textile wire is made with a polymer adapted to high temperatures.

In particular, the step of electric connection of an electric resistance measuring device comprises the steps of:

welding the first electric cable to the mesh portion A for connecting it electrically to the first end;

welding the second electric cable to the mesh portion C for connecting it electrically to the second end.

Advantageously, a step is also provided of arranging an auxiliary conductive insulated wire on a fourth thread-guide of the linear knitting machine, said auxiliary conductive insulated wire having an auxiliary first end and an auxiliary second end.

In particular, are also provided the steps of:

meshing simultaneously the auxiliary conductive insulated wire with the non-insulated conductive wire and the conductive insulated wire at the mesh portion A;

meshing simultaneously the auxiliary conductive insulated wire with the textile wire and the conductive insulated wire at the mesh portion B;

meshing simultaneously the auxiliary conductive insulated wire with the non-insulated conductive wire for making a mesh portion B, said mesh portion E having conductive surface;

connecting by welding the conductive insulated wire with the auxiliary conductive insulated wire at the mesh portion A for connecting electrically the first end to the auxiliary first end;

connecting by welding the auxiliary conductive insulated wire with the non-insulated conductive wire at the mesh portion E for connecting electrically the auxiliary second end to the mesh portion E.

In particular, the step of electric connection of an electric resistance measuring device comprises the steps of:

welding the first electric cable to the mesh portion C for connecting it electrically to the second end;

welding the second electric cable to the mesh portion E for connecting it electrically to the auxiliary second end.

This way, the length of the conductive insulated wire is doubled, further increasing the sensitivity to the resistance variations.

In particular, a step is also provided of meshing simultaneously the auxiliary conductive insulated wire with the textile wire for making a mesh portion D having electric not conductive surface, said mesh portion D located between the mesh portions C and E for electrically insulating them to each other.

Advantageously, a step is also provided of meshing simultaneously a heating wire in the mesh portion B of the textile temperature sensor, said heating wire arranged to generate heat for Joule effect.

This way, knowing the temperature in still air reached by the sensor when it is heated by the heating wire, it is possible to know the temperature excursion owing to the convection caused by the fluid that crosses the sensor and, consequently, it is possible to know the speed of the fluid itself. The temperature sensor can thus work also by anemometer.

BRIEF DESCRIPTION OF THE DRAWINGS

Further characteristic and/or advantages of the present invention are more bright with the following description of an exemplary embodiment thereof, exemplifying but not limitative, with reference to the attached drawings in which.

DESCRIPTION OF SOME PREFERRED EXEMPLARY EMBODIMENTS

Figure 2:
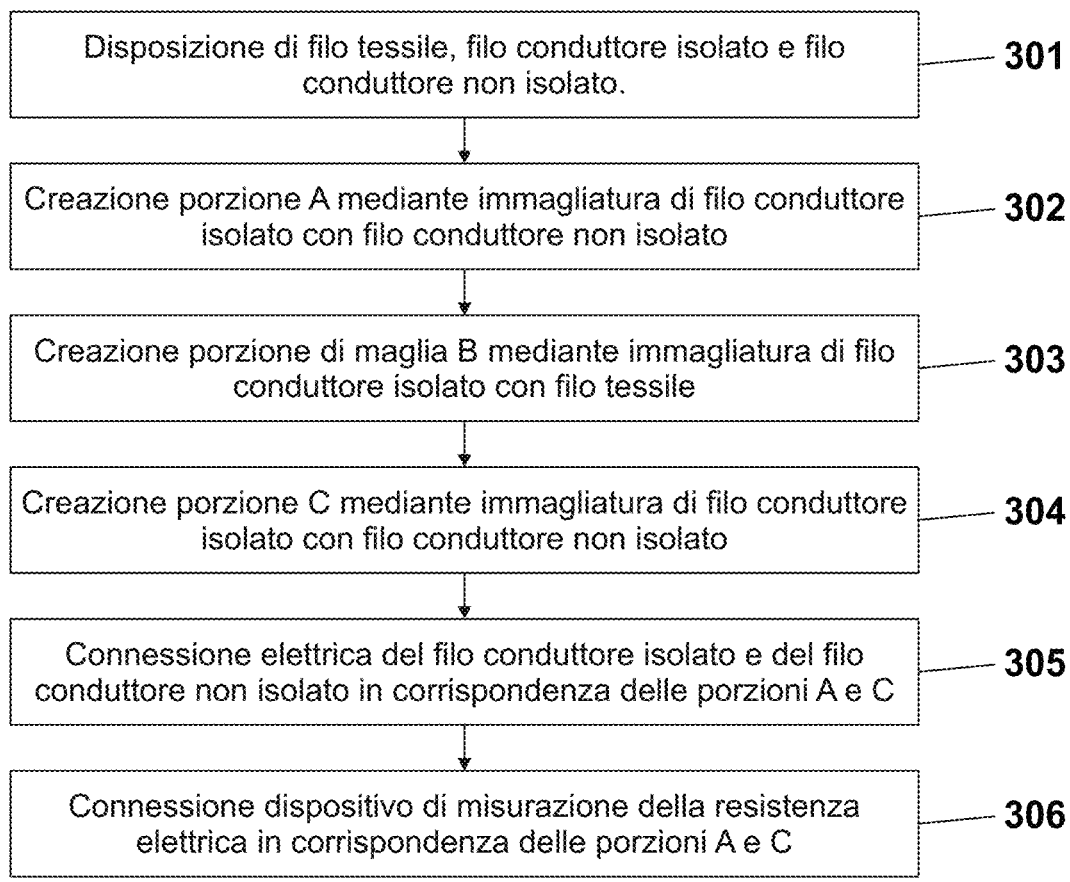
FIG. 2 shows a block diagram of the method, according to the present invention, used to generate an exemplary embodiment of the temperature sensor of FIG. 4.
Figure 4:
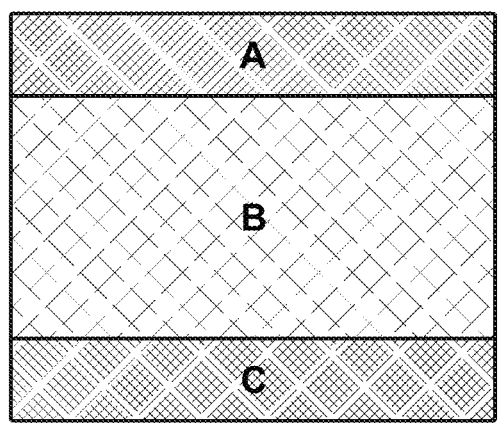
FIG. 4 shows a first exemplary embodiment of the temperature sensor made with the method according to the present invention.

In FIG. 2 schematically shows the steps of the method necessary, according to the present invention, to generate the textile temperature sensor 100 of FIG. 4.

In particular, in a preliminary step [301] a textile wire 110, a conductive insulated wire 120 and a non-insulated conductive wire are arranged on respective thread-guides of a linear knitting machine. The conductive insulated wire 120 can be, for example, an enameled copper wire, whereas the non-insulated conductive wire can be, for example, a tinned copper wire. The textile wire 110 can be, for example, a polyester wire.

Then you proceed meshing the wires. With reference to FIGS. 2 and 4, following the generation of the portions from A to C, you have the following steps of meshing:
  portion A: meshing conductive insulated wire 120 and non-insulated conductive wire [302];
  portion B: meshing conductive not insulated and textile wire 110 [303];
  portion C: meshing conductive insulated wire 120 and not non insulated conductive wire [304].

Once made the fabric as described above, you proceed to the electric connection of the conductive insulated wire 120 and of the non-insulated conductive wire at the portions A and C [305]. Such step can be made, for example, by welding, in order to dissolve locally the insulator coating the conductive insulated wire 120. Thus, the portions A and C, having conductive surface owing to the meshing of the non-insulated conductive wire, can work as poles for connecting the cables 201 and 202 of an electric resistance measuring device that causes passage of current in the conductive insulated wire 120 that crosses all the portions A, B and C, and allows finally to calculate the variation of resistivity and therefore the variation of temperature.

Figure 1:
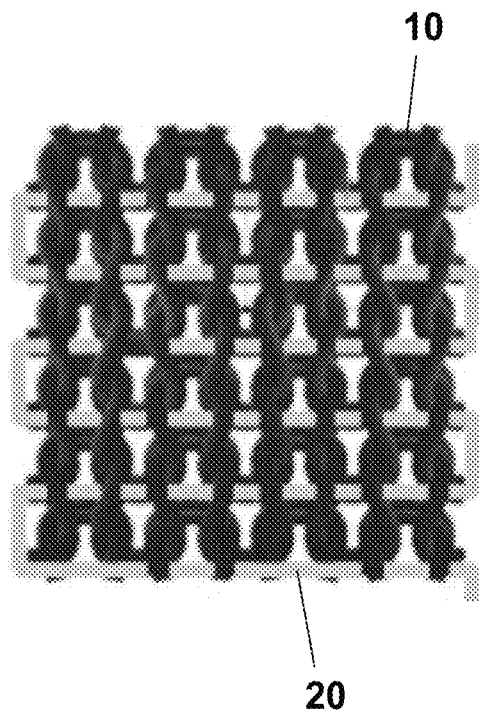
FIG. 1 shows the weaving technique used in a textile sensor of the prior art.
Figure 1A:
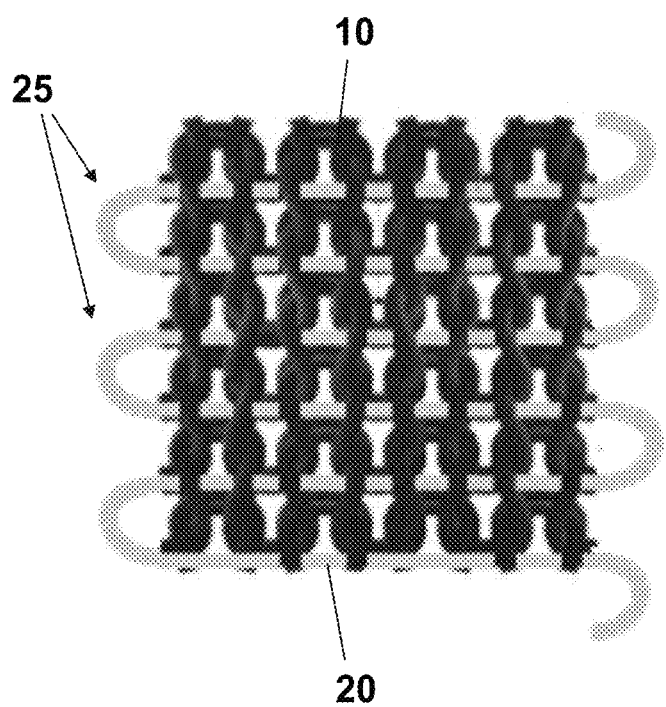
FIG. 1A shows the side slots which may form in the sensor of FIG. 1.
Figure 3:
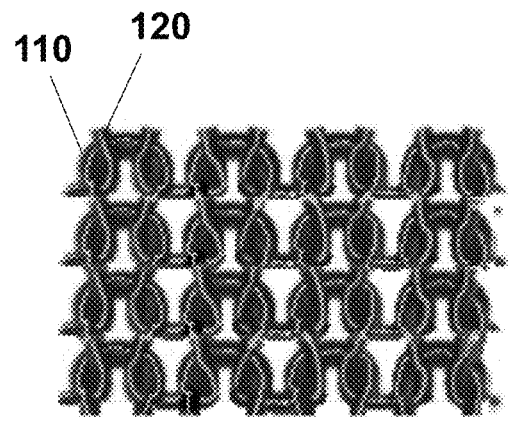
FIG. 3 shows the meshing technique used in the method according to the present invention to overcome the difficulties of the prior art.

With reference to FIG. 3, you can see the difference between the meshing technique, used in above mentioned steps, and the weaving technique, used in prior art of FIG. 1. In particular, the meshing technique makes the wires 110 and 120 substantially overlapped in all the mesh.

Owing to this there are many advantages, since it is possible to cause the conductive insulated wire 120 making a path higher than the prior art, increasing l and therefore improving the sensitivity in detecting the temperature, as explained in the section of the prior art. Furthermore, the textile structure derived from this technique is much more adapted to withstand strain and tension, since the textile wire 110 and the conductive one are substantially overlapped throughout the mesh, giving them a similar elasticity, contrarily to the prior art. Such aspect, in addition to improve the elasticity and the resistance of the textile sensor, allows also to reduce the cross section A of the conductive wire, further improving the sensitivity in detecting the temperature.

Furthermore, the presence of the portions A and C allows a steadier welding of the cables of the electric resistance measuring device to the conductive insulated wire 120, since the cables can be welded to an entire conductive area, rather than to the at the ends of a metal wire, as provided in prior art.

Figure 5:
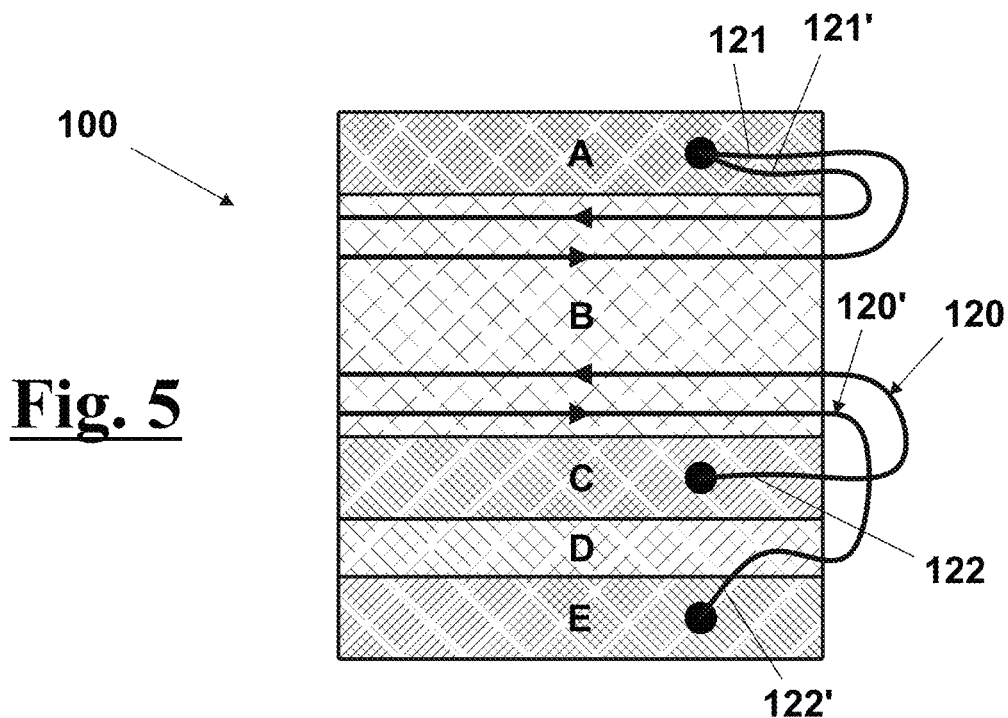
FIG. 5 shows a second exemplary embodiment of the temperature sensor where the conductive wire has doubled length.

With reference to FIG. 5, for increasing further the length l of the conductive insulated wire 120, it is possible to add an auxiliary conductive insulated wire 120', to connect to the conductive insulated wire 120, to the respective ends 121 and 121', at the mesh portion A.

In particular, following the generation of all the portions from A to E, you have the following steps of meshing:
  portion A: meshing conductive insulated wire 120, auxiliary conductive insulated wire 120' and non-insulated conductive wire;
  portion B: meshing conductive insulated wire 120, auxiliary conductive insulated wire 120' and textile wire 110;
  portion C: meshing conductive insulated wire 120 and non-insulated conductive wire;
  portion D: meshing auxiliary conductive insulated wire 120' and textile wire 110;
  portion E: meshing auxiliary conductive insulated wire 120' and non-insulated conductive wire.

You have then a step of welding the ends 122 and 122', respectively, in the portions C and E that become the conductive areas to which can be connected the ends of the electric resistance measuring device. Since the cables are typically connected by welding, i.e. dissolving the insulating coating of the wire insulated 120 to allow it to enter in electric connection with the non-insulated conductive wire of the portion C, in this portion cannot be meshed also the auxiliary conductive insulated wire 120', otherwise would occur a short circuit. The auxiliary conductive insulated wire 120' must then has to be placed on the side in the portion C and then start again to be meshed by the portion D. Alternatively, the conductive insulated auxiliary 120' can start again to be meshed directly in the portion. E and the portion D can be a mesh portion only with the textile wire 110.

The portion D that has surface not conductive since there is not the non-insulated conductive wire, allows instead to insulate to each other the portions C and E, avoiding short circuits.

This exemplary embodiment allows to double the conductive insulated wire, further improving the sensitivity in detecting the temperature. Furthermore, it is a solution more practical, since it determines to have connection areas for the connection of the electric resistance measuring device close to each other.

In the solution of FIG. 5, in the portions A and B are meshed three wires at the same time. In case that the machine is not adapted to operate with more than 2 thread-guide at the same time on each knitting row, it is possible to operate to alternated rows, meshing only two wires per row. For example, for portion A it is possible to alternate the following rows:
row 1: meshing non-insulated conductive wire and conductive wire 120;
row 2: meshing non-insulated conductive wire and auxiliary conductive wire 120'.

Figure 6:
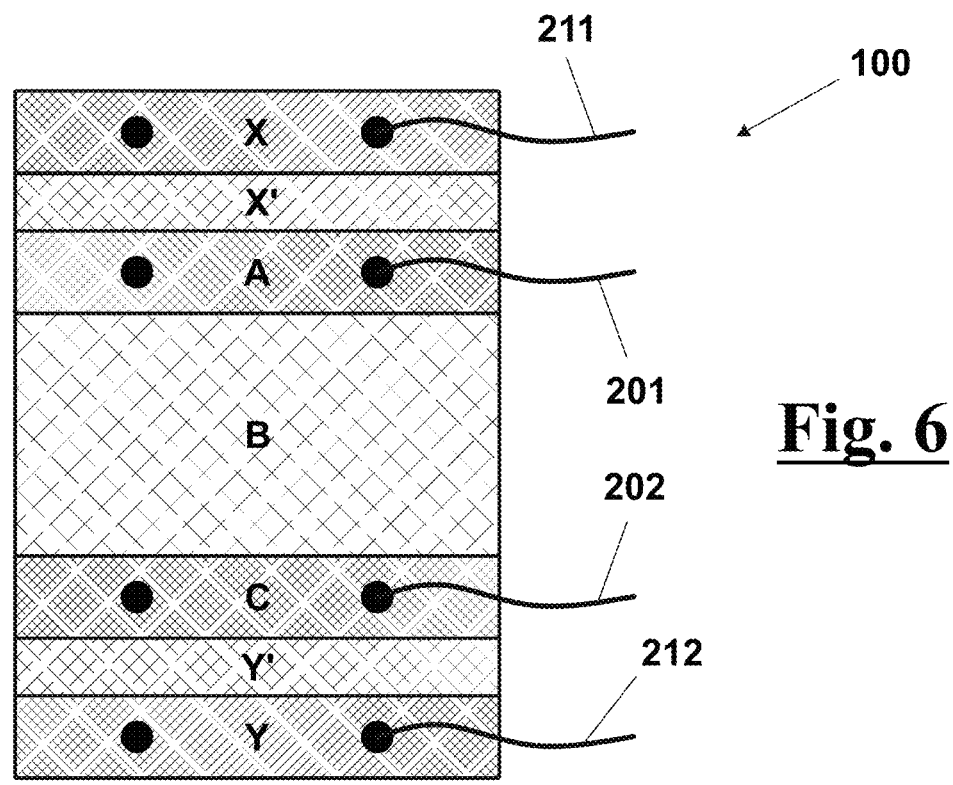
FIG. 6 shows a third exemplary embodiment of the temperature sensor where it is present a heating wire in parallel in order to provide a heat wire anemometer.

With reference to FIG. 6, in a further exemplary embodiment, it is possible to mesh a heating wire with the textile sensor shown in FIG. 4, by making a circuit parallel to that of thermoresistor.

In particular, following the generation of all the portions from X to Y, you have the following steps of meshing:
portion X: meshing non-insulated conductive wire and heating wire;
portion X': meshing textile wire 110;
portion A: meshing conductive insulated wire 120, non-insulated conductive wire;
portion B: meshing conductive insulated wire 120, textile wire 110 and heating wire;
portion C: meshing conductive insulated wire 120, non-insulated conductive wire;
portion Y': meshing textile wire 110;
portion Y: meshing not non-insulated conductive insulated wire and heating wire.

To portions A and C are connected, in a way completely similar to an exemplary embodiment of FIG. 4, the cables 201 and 202 of the electric resistance measuring device. To the portions X and Y (insulated by the portions A and C by the portions X' and Y' having not conductive surface) are instead connected the cables 211 and 212 of a separated supplier arranged to heat the heating wire for Joule effect.

Like what said above, the heating wire cannot be meshed in the mesh portions A and C, otherwise, at welding the cables 201 and 202, would occur an electric connection between the heating circuit and the thermoresistor circuit, which instead must act in parallel. In such portions, therefore, the heating wire is left out of the tissue and meshed only in the portion B. In the portions X' and Y' the heating wire can be meshed or not, according to the particular reasons, without affecting in any way the functionality of an exemplary embodiment described.

Owing to the presence of the heating circuit, knowing the temperature at which comes the sensor heated by the heating wire when the fluid has speed zero, it is possible to know the temperature excursion owing to the convection caused by the fluid that crosses the sensor and, consequently, it is possible to know the speed of the fluid itself. The temperature sensor can, thus work also by anemometer. It is possible, for example, to use this sensor on the section of a duct where air or other fluid flows to detect its speed at that point.

Figure 7:
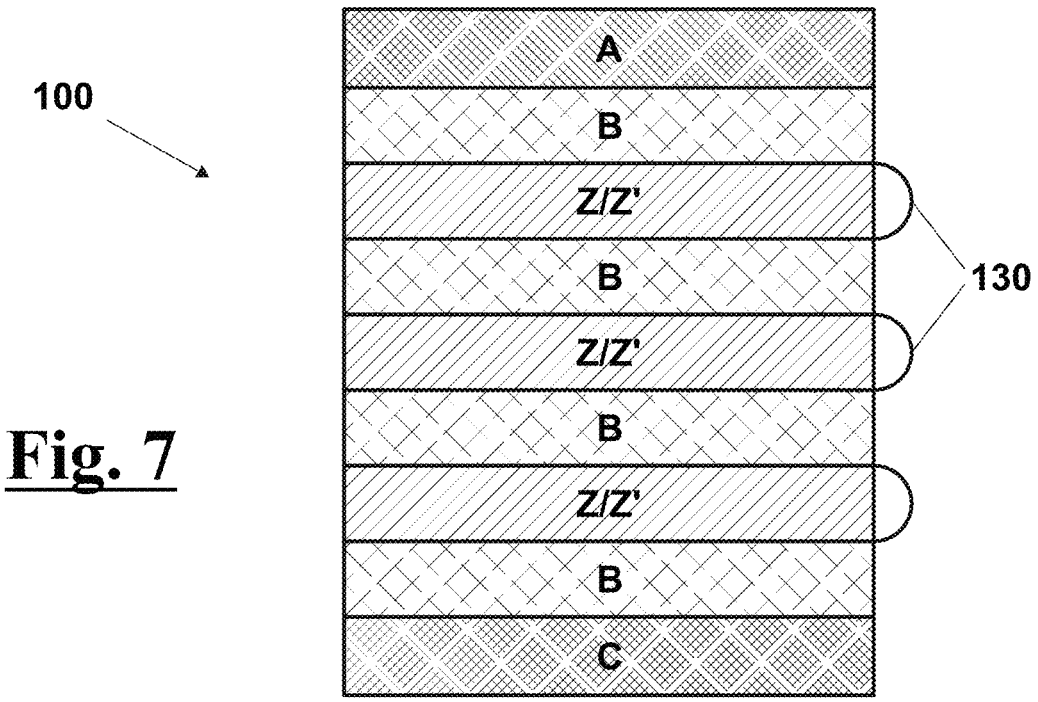
FIG. 7 shows an exemplary embodiment of the temperature sensor where they are integrated strips meshed with piezoresistive wire.

In FIG. 7 an exemplary embodiment is shown of the textile temperature sensor 100 of FIG. 4, wherein a plurality is provided of strips of mesh portions B alternate to strips of mesh portions Z. The mesh portions B are to each other electrically connected by the joints 130. The mesh portions Z are instead made by meshing a wire of piezoresistive material and are overlapped to corresponding strips of mesh portion Z' made by meshing non-insulated conductive wire.

Figure 8:
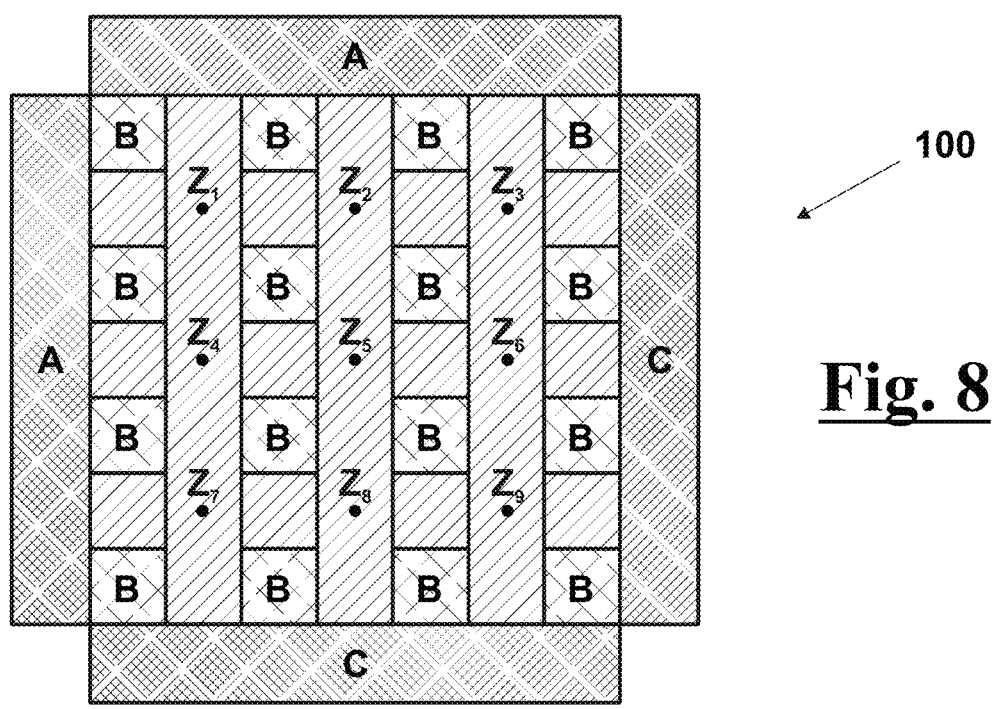
FIG. 8 shows a schematic exemplary embodiment where the temperature sensor works also as pressure sensor owing to the presence of crossed strips meshed with piezoresistive wire.

With reference even at FIG. 8, superimposing and arranging to 90° two exemplary embodiments of the sensor 100 of FIG. 7, it is possible to obtain a sensor 100 configured to work both from temperature sensor and pressure sensor. In fact, owing to the crossing of the strips Z and to the presence of strips Z' conductive or semiconductive it is possible to determine points of pressure $Z_i$ on which, by arranging a pressure, there is changing resistivity of the piezoresistive wire, allowing to calculate the amount of the pressures acting on the points $Z_i$ itself. This way, it is possible to analyze a map of pressures acting on the sensor 100 that, in this exemplary embodiment, then allows measuring both the temperature than the pressure.

Furthermore, both exemplary embodiment of FIG. 7 and of FIG. 8, the sensor 100 allows measuring the temperature in a way further localized, since it is possible, by means of special electric connections, to receive data of change of the resistivity by a single strip B or also by the crossing points, in FIG. 8, between strips B to each other overlapped and perpendicular.

The foregoing description some exemplary specific embodiments will so fully reveal the invention according to the conceptual point of view, so that others, by applying current knowledge, will be able to modify and/or adapt in various applications the specific exemplary embodiments without further research and without parting from the invention, and, accordingly, it is meant that such adaptations and modifications will have to be considered as equivalent to the specific embodiments. The means and the materials to realise the different functions described herein could have a different nature without, for this reason, departing from the field of the invention. it is to be understood that the phraseology or terminology that is employed herein is for the purpose of description and not of limitation.

The invention claimed is:

1. A method for manufacturing a textile temperature sensor, comprising:
arranging a linear knitting machine comprising at least one first thread-guide and a second thread-guide;
arranging a conductive insulated wire on said first thread-guide, said conductive insulated wire having a first end and a second end;
meshing said conductive insulated wire for making at least one mesh portion B having a non-conductive surface;
arranging an electric resistance measuring device configured to measure a variation of electric resistance R(T), said electric resistance R(T) being a function of the temperature T, said electric resistance measuring device comprising a first electric cable and a second electric cable;
electric connection of said first electric cable to said first end and of said second electric cable to said second end;
arranging a control unit arranged to receive from said device said variation of electric resistance R(T) in order to calculate excursions of temperature T at said lead wire;
arranging a non-insulated conductive wire on said second thread-guide;
simultaneously meshing said conductive insulated wire with said non-insulated conductive wire for making two mesh portions A and C, said mesh portions A and C having conductive surfaces;
connecting said conductive insulated wire with said non-insulated conductive wire for electrically connecting said first end to said mesh portion A, and said second end to said mesh portion C;
wherein said step of electric connection of said first electric cable to said first end, and of said second electric cable to said second end is carried out connecting, respectively, said first electric cable to said mesh portion A, and said second electric cable to said mesh portion C.

2. The method according to claim 1, further comprising:
arranging a textile wire on a third thread-guide of said linear knitting machine; and
simultaneously meshing said textile wire with said conductive insulated wire at said at least one mesh portion B.

3. The method according to claim 1, wherein said step of connection of said conductive insulated wire with said non-insulated conductive wire is made by welding.

4. The method according to claim 1, wherein said step of connection of said conductive insulated wire with said non-insulated conductive wire is made by removal of an insulator of said conductive insulated wire, said removal occurring, alternatively, by a member selected from the group consisting of:
a chemical process;
a mechanical abrasion;
a heat abrasion; and
a combination thereof.

5. The method according to claim 3, wherein said step of connection of said conductive insulated wire with said non-insulated conductive wire is carried out at said mesh portions A and C.

6. The method according to claim 1, further comprising the steps of:
defining a length l* of conductive wire on which measuring the resistance;
detection of connection points O and P such that said length l* is among said connection points O and P;
and wherein said step of connection of said conductive insulated wire with said non-insulated conductive wire is made at said connection points O and P.

7. The method according to claim 1, wherein said step of meshing said conductive insulated wire for making at least one mesh portion B is arranged to create a number n of mesh portions B, the method further comprising:
arranging a piezoresistive wire on a fourth thread-guide of said linear knitting machine;
meshing said piezoresistive wire for making a number n−1 of mesh portions Z;
said n mesh portions B and said n−1 mesh portions Z being displaced adjacent to each other, and alternate to each other.

8. The method according to claim 7, wherein a step is provided of meshing said non-insulated conductive wire for making a number n−1 of mesh portions Z' arranged to be overlapped to said n−1 mesh portions Z.

9. The method according to claim 1, wherein said step of electric connection of an electric resistance measuring device comprises the steps of:
welding said first electric cable to said mesh portion A for electrically connecting said mesh portion A to said first end; and
welding said second electric cable to said mesh portion C for electrically connecting said mesh portion C to said second end.

10. The method according to claim 1, further comprising arranging an auxiliary conductive insulated wire on a fourth thread-guide of said linear knitting machine, said auxiliary conductive insulated wire having an auxiliary first end and an auxiliary second end;
simultaneously meshing said auxiliary conductive insulated wire with said non-insulated conductive wire and said conductive insulated wire at said mesh portion A;
simultaneously meshing said auxiliary conductive insulated wire with said textile wire and said conductive insulated wire at said mesh portion B;
simultaneously meshing said auxiliary conductive insulated wire with said non-insulated conductive wire for making a mesh portion E, said mesh portion E having a conductive surface;
connecting, by welding, said conductive insulated wire with said auxiliary conductive insulated wire at said mesh portion A for electrically connecting said first end to said auxiliary first end; and
connecting, by welding, said auxiliary conductive insulated wire with said non-insulated conductive wire at said mesh portion E for electrically connecting said auxiliary second end to said mesh portion E.

11. The method according to claim 3, wherein said step of electrical connection of an electric resistance measuring device comprises the steps of:
welding said first electric cable to said mesh portion C for electrically connecting said mesh portion C to said second end;
welding said second electric cable to said mesh portion E for electrically connecting said mesh portion E to said auxiliary second end.

12. The method according to claim 11, wherein a step is also provided of simultaneously meshing said auxiliary conductive insulated wire with said textile wire for making a mesh portion D having an electric non-conductive surface, said mesh portion D located between said mesh portions C and E for electrically insulating them to each other.

13. The method for according to claim 1, wherein a step is also provided of simultaneously meshing a heating wire in said mesh portion B of said textile temperature sensor, said heating wire arranged to generate heat for a Joule effect.

* * * * *